United States Patent [19]

Moore

[11] Plant 4,495

[45] Jan. 22, 1980

[54] MINIATURE ROSE PLANT

[76] Inventor: Ralph S. Moore, 2519 East Noble Ave., Visalia, Calif. 93277

[21] Appl. No.: 963,575

[22] Filed: Nov. 24, 1978

[51] Int. Cl. ..... A01H 5/00
[52] U.S. Cl. ..... Plt./7
[58] Field of Search ..... Plt./7

*Primary Examiner*—Robert E. Bagwill

[57] ABSTRACT

The subject of the present described invention is a new and distinct variety of miniature rose plant characterized by small double flowers of a mixture of colors, being primarily shades of red and white in varying patterns or stripes and a plant similar to but more vigorous and with more stocky canes than Stars'N Stripes.

7 Drawing Figures

1

The present invention relates to a new and distinct variety of hardy, dwarf, bush or shrub type rose plant of the miniature class: the variety being primarily characterized—as to novelty—by striped or variegated flowers which in general color effect are similar to Stars'N Stripes (miniature—U.S. Plant Pat. No. 4,029).

The variety is further characterized by:

An abundance of bloom, with flowers borne singly or several to the stem in loose clusters.

Light mossing on buds (sepals).

Little or no fragrance.

A plant which is vigorous, of rounded spreading shape with small semi-glossy to matt foliage with pointed leaflets; the buds and flowers being similar in form and size to Over The Rainbow (miniature—U.S. Plant Pat. No. 3,472).

The plant, which has a normal height of 12–16 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Little Darling, Floribunda (U.S. Plant Pat. No. 1,581, expired) as the seed parent and un-named seedling #33 (miniature—not patented) as the pollen parent.

Subsequent to origination of the variety I successfully asexually reproduced it, in my nursery located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; rounded spreading habit; seedling; greenhouse; outdoors; cut flowers; garden decoration; potted plant.

Class: Miniature.

Variety name: Strawberry Swirl.

Flowers borne: Singly and several together (3 to 5) on slender wirey stems.

2

Quantity of bloom: Abundant both outside and in greenhouse.

Bud:

*Peduncle.*—Medium length; slender but sturdy; erect; medium green, sometimes tinted bronze (outdoors); hairs — many short hairs and soft thorns. *Before calyx breaks*—size — small. Form slender — ovid: pointed with several small foliaceous appendages and several to fairly numerous very short hairs (light mossing) on surface of bud; with foliaceous parts extending beyond the tip of the bud equal to less than one-half of its length. Color — medium green, occasionally tinted with bronze (outdoors).

*As calyx breaks.*—Color — usually red — near Cardinal Red 822/2 but may show some white areas or stripes. Opening: opens well in all weather.

Bloom:

*Size when fully open.*—Small, averaging about 30–35 mm ($1\frac{3}{8}''$).

*Petalage.*—Double — averaging about 50 petals, arranged regularly plus sometimes several small petaloids.

*Form.*—Cupped at first, then becoming more rounded and high centered, with petals rolled loosely outward, and later at maturity full and rather rounded with outer petals often folded at edge to give a pointed effect and rolled loosely outward and downward. Open flower full, rounded, sometimes may show stamens.

Petals: Fairly thick; satiny on inside and on outside surface.

*Shape.*—Outside petals, broad lanceolate (nearly round) with rounded tip; intermediate — broad lanceolate with rounded tip; inside — lanceolate with short acute tip.

Color: Newly opened flower from a plant grown in plastic greenhouse (October 1978), Visalia, Calif.:

*Outside petal.*—Outside surface — near Crimson 22/1 with both lighter and darker areas (plus occasional white or near white stripes) becoming near white at base. Inside surface — near Rose Madder 23/1 (with both lighter and darker areas (plus occasional white or near white stripes) becoming near white at base.

*Intermediate petal.*—Outside surface — near Crimson 22/2 (with occasional stripes) becoming near white at base. Inside surface near Rose Madder 23/1 similar to outside petal.

*Inner petal.*—Outside surface similar to intermediate petal; inside surface — similar to intermediate petal. General color effect; newly opened flowers — red and white variegation of differing patterns and differing shades of color, depending upon maturity of flowers, time of year, intensity of sunlight and whether growing inside greenhouse or outside.

Note: The red shades described above are from flowers grown in plastic house in October, 1978. The flowers shown in color photo are lighter (more pink) and taken from same plants in same greenhouse in August, 1978. Three days open — color similar to newly opened flowers. Behavior — opens well in all weather. Color darker red outdoors. Spent petals drop off. Flower longevity (June 1978) — plant in pot 6–8 days or longer. Cut flowers at living room temperature 5–7 days.

Reproductive Organs:

*Stamens.*—Few or none, if present, arranged irregularly about pistils.

*Filaments.*—Varying length, short, near white.

*Anthers.*—May be well formed or malformed; pinkish.

*Pollen.*—Little or none.

*Pistils.*—Few; often malformed.

*Styles.*—Varying length; bunched; color — greenish.

*Ovaries.*—All enclosed in calyx.

*Hips.*—Few — usually none.

*Sepals.*—Permanent; spear shaped; recurved.

*Seed.*—Few — usually none.

Foliage:

*Leaves.*—Compound of five (sometimes three or seven) leaflets; small; leathery; semi-glossy to matt.

*Leaflets.*—Shape: broad, nearly oval (egg shape); apex acute; base rounded or rounded acute. Margin serrate. Color: medium green; new growth — reddish. Rachis: medium strength; upper side may have several to many tiny short prickles or hairs, grooved; underside; several thorns with several to numerous tiny prickles and thorns. Stipules: medium long; medium width; short to medium narrow points which turn out at more or less than 45°.

Growth:

*Habit.*—Dwarf; bushy; spreading; much branched.

*Growth.*—Free vigorous; internodes short.

*Canes.*—Medium; slender; sturdy.

*Main stems.*—Color: medium green.

*Thorns.*—Many of varying length and size; slender; usually straight but inclined slightly downward; color; brown. Prickles — some. Hairs: may be some.

*Branches.*—Color: Medium green. Thorns: numerous; varying length and size; slender; nearly straight, but inclined slightly downward. Medium to short oval base. Prickles: some. Hairs: may be some.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, compact, spreading much branched habit, substantially as illustrated and described, characterized by buds and flowers which are (A) variegated or striped in varying shades of red and white, the bud and flower resembling Stars'N Stripes miniature (Plant Pat. No. 4,029) in size and shape but with more petals; and (B) further characterized by a plant which is vigorous, of compact spreading habit, easy to propagate from cuttings or by budding, with an abundance of small size semiglossy to matt foliage and an abundance of flowers borne singly or several to the stem in loose clusters.

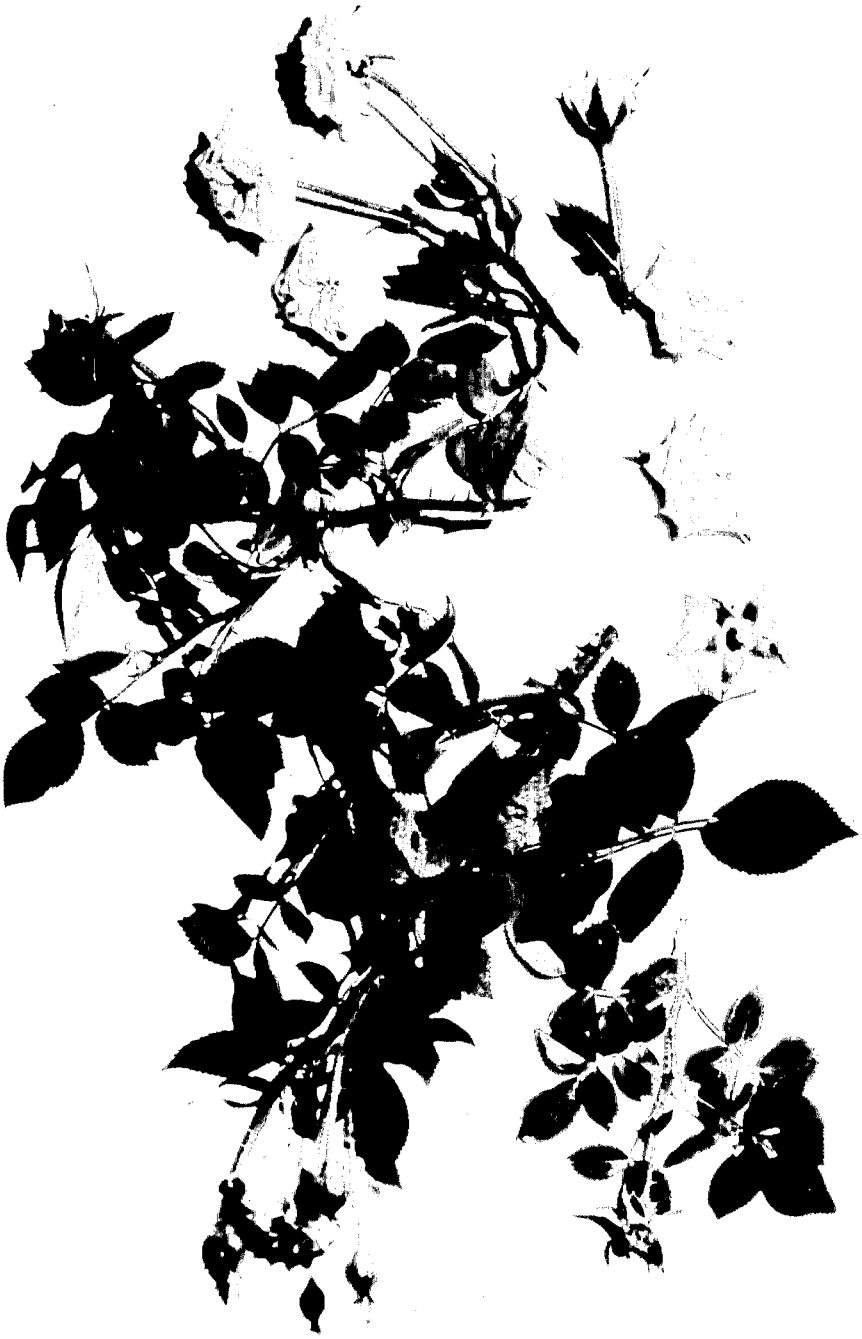

* * * * *